US012496016B2

(12) United States Patent
Deslauriers et al.

(10) Patent No.: US 12,496,016 B2
(45) Date of Patent: Dec. 16, 2025

(54) PATIENT POSITIONING DEVICE

(71) Applicant: Contract Medical Manufacturing LLC, Oxford, CT (US)

(72) Inventors: Richard Deslauriers, Woodbury, CT (US); Patrick Brandon, Killingworth, CT (US); Rodrigo DaSilva, Trumbull, CT (US)

(73) Assignee: Contract Medical Manufacturing LLC, Oxford, CT (US)

( * ) Notice: Subject to any disclaimer, the term of this patent is extended or adjusted under 35 U.S.C. 154(b) by 389 days.

(21) Appl. No.: 18/096,632

(22) Filed: Jan. 13, 2023

(65) Prior Publication Data

US 2023/0233150 A1 Jul. 27, 2023

Related U.S. Application Data

(60) Provisional application No. 63/301,557, filed on Jan. 21, 2022.

(51) Int. Cl.
*A61B 5/00* (2006.01)

(52) U.S. Cl.
CPC .................................... *A61B 5/702* (2013.01)

(58) Field of Classification Search
CPC ...... A61B 5/702; A61G 13/12; A61G 13/121; A61G 13/1225; A61G 13/1285; A61G 13/123; A61G 13/1235; A47C 27/12; A61F 5/3723
USPC .......................................... 5/81.1 T; 128/845
See application file for complete search history.

(56) References Cited

U.S. PATENT DOCUMENTS

| | | | | |
|---|---|---|---|---|
| 6,966,081 | B1 | 11/2005 | Sharps et al. | |
| 8,464,720 | B1 | 6/2013 | Pigazzi et al. | |
| 8,511,314 | B2 | 8/2013 | Pigazzi et al. | |
| 8,636,680 | B2 | 1/2014 | Hiebert | |
| 9,375,343 | B2 * | 6/2016 | Marshall | A61G 13/1225 |
| 9,750,656 | B1 | 9/2017 | Pigazzi et al. | |
| 10,842,206 | B2 | 11/2020 | Kaforey et al. | |
| 11,266,525 | B2 | 3/2022 | Kaforey et al. | |
| 11,484,456 | B2 | 11/2022 | Pigazzi et al. | |
| 11,510,836 | B2 * | 11/2022 | Cole | A61G 13/127 |
| 2022/0110809 | A1 * | 4/2022 | Grindstaff | A47C 27/14 |
| 2022/0142805 | A1 * | 5/2022 | Zaganelli | A61F 5/3723 |
| 2022/0183874 | A1 | 6/2022 | Marshall et al. | |

FOREIGN PATENT DOCUMENTS

EP 2802305 10/2017

OTHER PUBLICATIONS https://www.xodusmedical.com—The Pink Pad Air-Assist.

* cited by examiner

*Primary Examiner* — David R Hare
*Assistant Examiner* — Joseane E. Tejada
(74) *Attorney, Agent, or Firm* — Neil D. Gershon

(57) ABSTRACT

A patient positioning device attachable to a medical table comprising a base configured to overlie the table and underlie the patient, wherein the upper surface of the base faces the patient and the lower surface faces the table. One or more supports are removably attachable to the base to support a body region of the patient. The base can be composed of a foam material with a covering material for removable attachment of the supports. Various shapes, sizes and function of the supports can be used.

19 Claims, 17 Drawing Sheets

PATIENT POSITIONING DEVICE

This application claims priority from U.S. provisional application 63/301,557, filed Jan. 21, 2022, the entire contents of which are incorporated herein by reference.

BACKGROUND

Field of the Invention

This application relates to a patient positioning device, and, more particularly, to a patient positioning device attachable to an operating table to help secure the patient.

Background

During various surgical procedures, patients are placed in different positions on the operating table such as a supine position, an inclined position, a reverse inclined position, a Trendelburg position (feet above the head), reverse Trendelburg position (tilted with head above the feet), etc. Several patient positioning devices of the prior art have been developed which are attachable to the operating table to help support the patient in the various positions. Their objective is to support the patient as well as restrain and/or immobilize the patient. However, each of these prior art devices suffers one or more drawbacks such as limited versatility, compromised patient comfort, inadequate patient restraint, costly and/or difficult to manufacture, etc.

The need exists for an improved patient positioning device that provides increased comfort and improved patient restraint and enables better accommodation of patients of various sizes and in different positions on the operating table.

SUMMARY

The patient positioning devices of the present invention overcome the problems and deficiencies of the prior art. The patient supporting devices of the present invention are placed on a medical table such as an operating table for supporting a patient in different positions. In some embodiments, the devices include a pad with bendable portions to form patient supports and limit movement of the patient on the operating table. In such embodiments, the bendable portions can also be utilized to attach the base to the medical table. In other embodiments, the devices include a pad for mounting a variety of patient supports that are preferably removably attachable to the pad. The devices of the present invention have several advantageous features that enhance accommodation of patients of various sizes and in different positions on the operating table. The devices also have features providing increased versatility for attachment to the operating table as well as for securement of the patient to the table and support for various body regions of the patient. Each of these features are discussed in detail below.

In accordance with one aspect of the present disclosure, a patient positioning device attachable to a medical table such as an operating table or bed is provided. The patient positioning device comprises a base having an upper surface, a lower surface, a top region at a first portion, a bottom region at a second portion, a right side region and a left side region. The base is configured to overlie the table and underlie the patient, wherein the upper surface of the base faces the patient and the lower surface faces the table. One or more supports are selectively removably attachable to the base to support a body region of the patient.

The supports can be of various sizes and shapes, and for various functions such as lumbar support, head or neck rest, shoulder support, etc. For example, the support(s) can comprise an arm rest removably attachable to one or both of the right or left side regions of the base, a head rest removably attachable to the top region of the base, a lumbar support attachable to a middle region, etc.

In some embodiments, the base is made of a foam material and one or more portions of the base are bendable to form one or more bendable portions for attachment to a rail of the medical table. A support wire can be positioned within the bendable region to maintain a bent position of the bendable portion. The bendable portions in some embodiments can also be bent to provide arm or other body region support. In some embodiments, the bendable portions can be bent into a rolled position. The support wire in some embodiments is embedded in the foam material.

In some embodiments, the positioning device has a metal support attached to the base which is bendable to attach to the table. In some embodiments, the metal support is a single piece of metal; in other embodiments, the metal support comprises two or more metal members that are attached together. In either case, the metal support in such embodiments can extend along a length and a width of the base and can be arranged in an H-shape (longitudinal region and one or more transverse regions), a figure eight, X-shape or other shapes. In some embodiments, the metal support extends beyond right and left sides of a periphery of the base and are covered by a protective material. The protective material can be the same as the base and in some embodiments is a foam material.

In some embodiments, the base is asymmetric; in other embodiments, the base is symmetric so it can be positioned on the table in either direction and either side, i.e., the top and bottom regions are the same and the left and right side regions are the same.

In some embodiments, the positioning device includes a covering material covering at least a majority portion of the base to provide a Velcro friendly material for removable attachment of the supports to the Velcro friendly material.

In some embodiments, the base forms a first base and the device includes a second base attached to the first base, the first and second bases composed of a foam material and the metal support is sandwiched between the first and second bases. In some embodiments, a second covering material covers at least a majority portion of the second base to provide a Velcro friendly material for removable attachment of the supports to the Velcro friendly material if the device is used on a side where the second covering material faces the patient, the first base providing for the removable attachment of the supports if the device is used on a side where the first covering material faces the patient.

In accordance with another aspect of the present invention, a patient positioning device attachable to a medical table such as an operating table or bed, is provided. The patient positioning device comprises a base forming a first layer having a top region at a first portion, a bottom region at a second portion, a right side region and a left side region, and configured to overlie the table and underlie the patient to provide a support for the patient. A covering forming a second layer overlies at least a majority portion of the base and is configured to receive at least one patient support for attachment thereto. In some embodiments, the covering material provides a Velcro attachment surface for the at least one patient support.

In some embodiments, the positioning device includes a third layer, preferably of the same material as the first layer, and a second covering material forming a fourth layer covering the third layer, the first and third layers attachable to each other wherein the third and fourth layers are exposed and provide a surface for contacting the patient and for receiving the patient support(s).

In some embodiments, the base can comprise a foam pad having a plurality of slits formed therein to form zones of differing response to loads.

In some embodiments, the positioning device can include an absorbent material positioned over the base to provide a high-water absorption rate.

In accordance with another aspect of the present invention, a patient positioning device attachable to a medical table is provided comprising a base having a top region at a first portion, a bottom region at a second portion, a right side portion and a left portion. The base is configured to underlie the patient to provide a support for the patient. A metal support is attached to the base, the metal support including one or more metal elements that extend along a length and a width of the base, the metal supports bendable for attachment to a rail of the table.

In some embodiments, the base is composed of a foam which includes a plurality of slits to form zones of differing response to loads. In some embodiments, the metal support has a first section extending from the top region to the bottom region and a second section transverse to the first region extending from the left side region to the right side region, and in some embodiments extends beyond the left and right side regions.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Figure 1A:
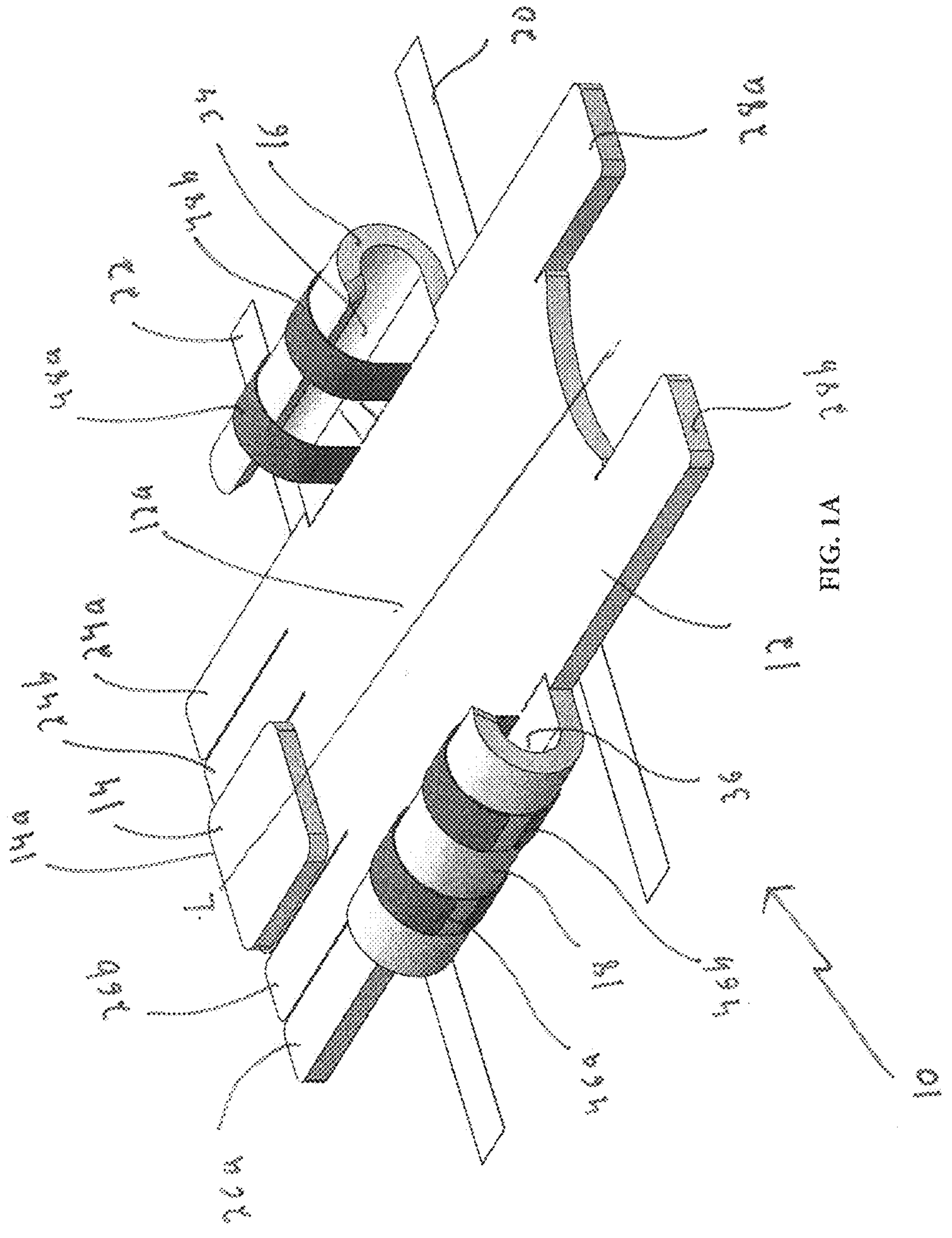
FIG. 1A is a perspective view of a first embodiment of the patient positioning device of the present invention, the side arm rest sections shown bent upwardly and the arm straps shown in the looped position to secure the bent side sections.

The present invention provides patient positioning devices that are attachable to a patient supporting structure such as an operating table or bed to support the patient on the table or bed. In some embodiments, the devices include pads with bendable portions to form patient supports and limit movement of the patient on the operating table. In other embodiments the devices include pads to provide a mount for a variety of patient supports which are removably attachable to the pads. The devices have several advantageous features that enhance accommodation of patients of various sizes and in different positions on the table as well as provide improved patient securement and improved patient restraint/stabilization in a cost effective manner.

In general, two versions of the devices are disclosed. In one version, the device is in the form of a pad with bendable portions which provide patient support and table mounting structure. In another version, the device is in the form of a pad onto which patient supports of various shapes, sizes and functions can be selectively, and preferably removably, attached. Each of the two versions have several alternative embodiments which are discussed in detail below.

The positioning devices of the bendable portion versions of the present invention (referred to herein for convenience as Version I) have several features to enhance patient comfort and/or securement and include one or more of the following: a) removable arm rests; b) bendable foam portions that are maintained in a bent condition; c) straps extending through the foam portions; d) foldable portions for shoulder comfort; and/or e) a slidable/repositionable head rest. Each of these features are discussed in detail below. Note that the positioning devices of the present invention can have all of the foregoing features a-e, or fewer than all such as one or two of these features, and still provide advantages over current patient positioning devices. Other features of the devices will become apparent from the discussion below.

The positioning devices of the mountable support versions of the present invention (referred to herein for convenience as Version II) have several features to enhance patient comfort and/or securement and include one or more of the following: a) modules removably attachable to the upper/top surface of the device where desired by the clinician to support and/or reposition the patient's body; b) a covering layer providing an increased mounting surface area for the modules; and c) a metal support attached to the base bendable to attach to the operating table to secure the device. Each of these features are discussed in detail below. Note that the positioning devices of the present invention can have all of the foregoing features a-c, or fewer than all such as one or two of these features, and still provide advantages over current patient positioning devices. Other features of the devices will become apparent from the discussion below.

Note that various features of one version can be used with the other version so the present invention is not limited to the features of the single version. For example, the bendable portion version (Version I) could include the metal support of Version II, the bendable Version I could include the removably attachable modules/supports of Version II, the bendable Version I could include the cover of Version II; the mountable support version (Version II) could include one or more of the bendable portions of Version I, etc.

The patient positioning devices of the present invention can advantageously be used to comfortably support and stabilize patients (provide stable positioning) on the operating table in various positions such as a supine position, an inclined position with respect to the horizontal, a reverse inclined (declined) position with respect the horizontal, a Trendelburg position (feet above the head), reverse Trendelburg position (tilted with head above the feet), etc. Other patient positions are also contemplated.

The positioning devices of the present invention can advantageously accommodate patients of varying BMI, e.g., thin, medium, and large.

The bendable sections of the positioning device of the bendable version described in detail below support and stabilize the patient and thus reduce or eliminate reliance on foam friction to stabilize the patient.

Referring now to the drawings and particular embodiments of the present invention wherein like reference numerals identify similar structural features of the devices disclosed herein, there are illustrated in FIGS. 1A-16 several embodiments of the patient positioning devices of the present invention. The positioning devices are configured for attachment to the operating table. FIGS. 1A-9 illustrate the bendable portion version (Version I) and FIGS. 11-16 illustrate the module attachment version (Version II). It should be appreciated that features of one version can be used with the other version.

With initial reference to FIG. 1A, the positioning device is designated generally by reference numeral 10 and includes a main base 12 which forms the main portion of the device 10 and is preferably composed entirely of foam or the core composed of foam, although other materials are also contemplated. The foam can be a memory foam and can be an open pore or closed pore design. A floating head rest 14 is removably positioned on the base 12 and can be repositioned along the top region of the base 12. Head rest 14 is shown as substantially rectangular in shape with a substantially planar upper surface, however, other configurations are also contemplated. Left arm section 16 and right arm section 18 extend outwardly (transversely) from the left and right side portions, respectively, of the base 12. In some embodiments, as described in detail below, the arm sections 16, 18 are removably attached to the base 12. Note the head rest 14 and left and right arm sections 16, 18, like the base 12, are preferably composed of a foam material.

Figure 3:
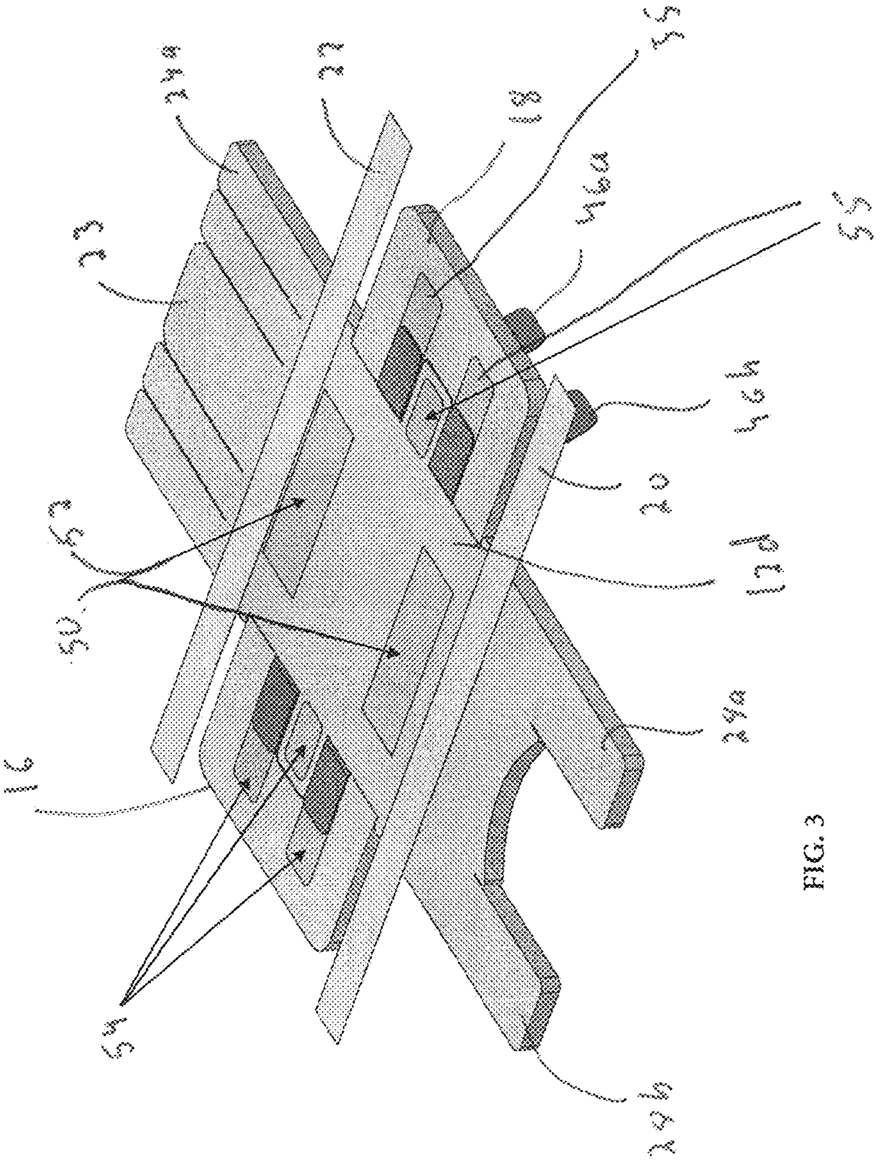
FIG. 3 is a perspective view showing the underside (lower/bottom surface) of the device of FIG. 1A.

Note, as used herein, the term "top" and "bottom" and "left" and "right" refer to the orientation corresponding to the position of the patient resting/lying on the positioning device. The patient lies facing upwardly, with the patient's back resting on upper surface 12*a* of base 12 and the patient's head at the "top" portion (region) of the base 12. Stated another way, the upper surface 12*a* faces the patient. The "lower" surface of the base 12, which rests against the top surface of the operating table (not shown), is shown in FIG. 3 and is designated by reference numeral 12*d*. Stated another way, the lower surface 12*d* of the base 12 faces the operating table. With the patient facing upwardly, the patient's right arm rests on, or is adjacent, "right" section 18 and the patient's left arm rests on, or is adjacent, "left" section 16. In preferred embodiments, the right and left sections are symmetrical, although asymmetrical configurations are also contemplated.

The bottom region (portion/section) of base 12 includes left and right extensions 28*a*, and 28*b*. These extensions (sections) are shown in the parallel position in FIGS. 1A, 2A and 2B, although non-parallel positions are also contemplated. In this parallel position, the extensions 28*a*, 28*b* are in a non-bent linear (planar) position. In the embodiment of these Figures, the extensions 28*a*, 28*b* are bendable downwardly toward the underlying operating table, out of the plane of the base 12, to help secure the bottom end of the foam base 12 to the operating table as it can engage a rail or the bed of the table. FIG. 1B, which illustrates an alternate embodiment of the positioning device as described below, shows the extensions 28*a*, 28*b* in the downwardly bent position, bent at regions 29*a*, 29*c* and terminating in ends 29*b*, 29*d*, respectively. The extensions 28*a*, 28*b* of FIG. 1A can be bent in a similar manner. The sections 28*a*, 28*b* in preferred embodiments are independently bendable although alternatively they can be co-joined to bend together. In some embodiments, the extensions 28*a*, 28*b*, can be bendable upwardly.

Figure 2A:
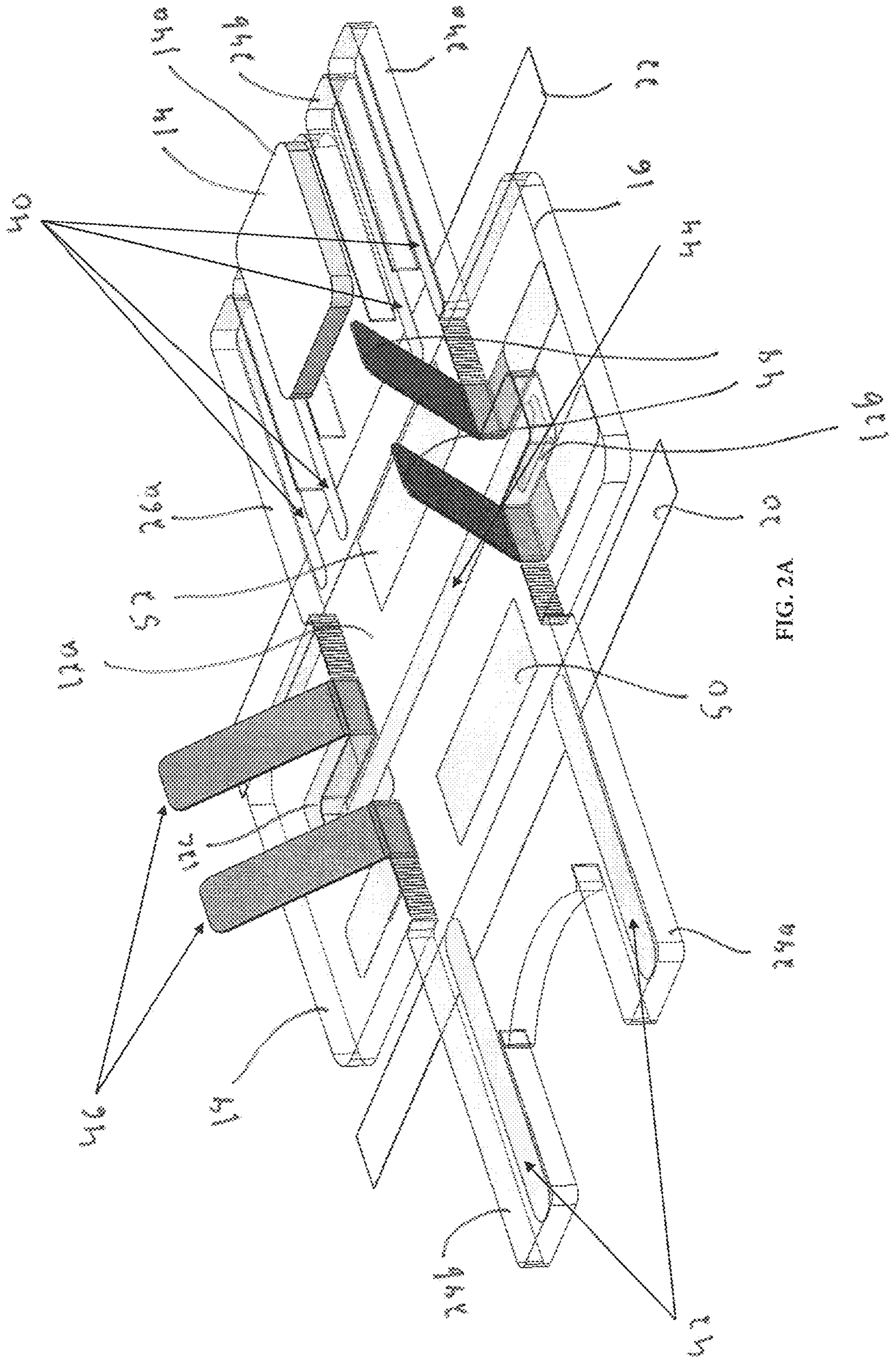
FIG. 2A is a perspective transparent view of the device of FIG. 1A, the device shown transparent to illustrate the metal strips and the friction pads on the underside (lower/bottom surface) of the base of the device, and the device shown with the side sections in the planar position.

Each bendable extension 28*a*, 28*b* includes a bendable metal strip 42 embedded (captured) inside the foam, shown in the transparent view of FIG. 2A. The metal strip 42 provides support to maintain the respective extension 28*a*, 28*b* in the bent position. In some embodiments, the metal strips 42 are 0.032 inches thick, although other dimensions are also contemplated. In the absence of such metal strips/metal supports, the foam material would not stay in the bent position and would tend to return towards (and potentially into) the straight/non-bent position of FIG. 1A.

Note in alternate embodiments, sections 28*a*, 28*b* are not bendable and remain in the linear/parallel position.

The top portion (region/section) of base 12 includes a pair of linear sections 24*a*, 24*b* on the left side of the head rest 14 and a pair of linear sections 26*a*, 26*b* on the right side of head rest 14. These sections 24*a*, 24*b*, 26*a*, 26*b* can be formed by elongated cuts in the foam which create these separate sections to enable independent bendability. In preferred embodiments, the sections 24*a*, 24*b*, 26*a*, 26*b* would extend slightly past the topmost edge (end) 14*a* of the head rest 14. In some embodiments, they can extend 6 inches past the topmost end 14*a*, although other lengths/distances are also contemplated, such as terminating flush with the topmost end 14*a* or terminating before the topmost edge 14*a*.

Note section 24*b* is inward of section 24*a* and section 26*b* is inward of section 26*a*, inward defined as closer to the central longitudinal axis L of the base 12.

Figure 1D:
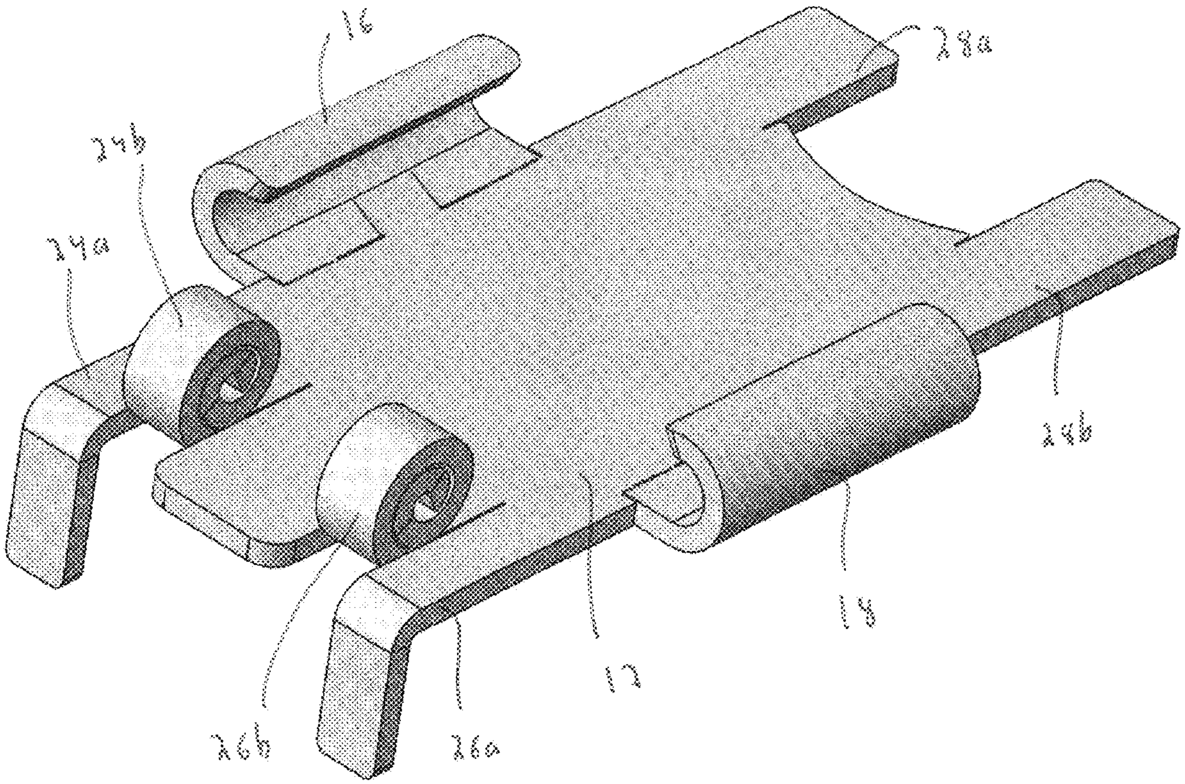
FIG. 1D is a perspective view illustrating the top (upper) outer sections of the base of FIG. 1A bent downwardly and the top (upper) inner sections of the base in a rolled position.
Figure 2B:
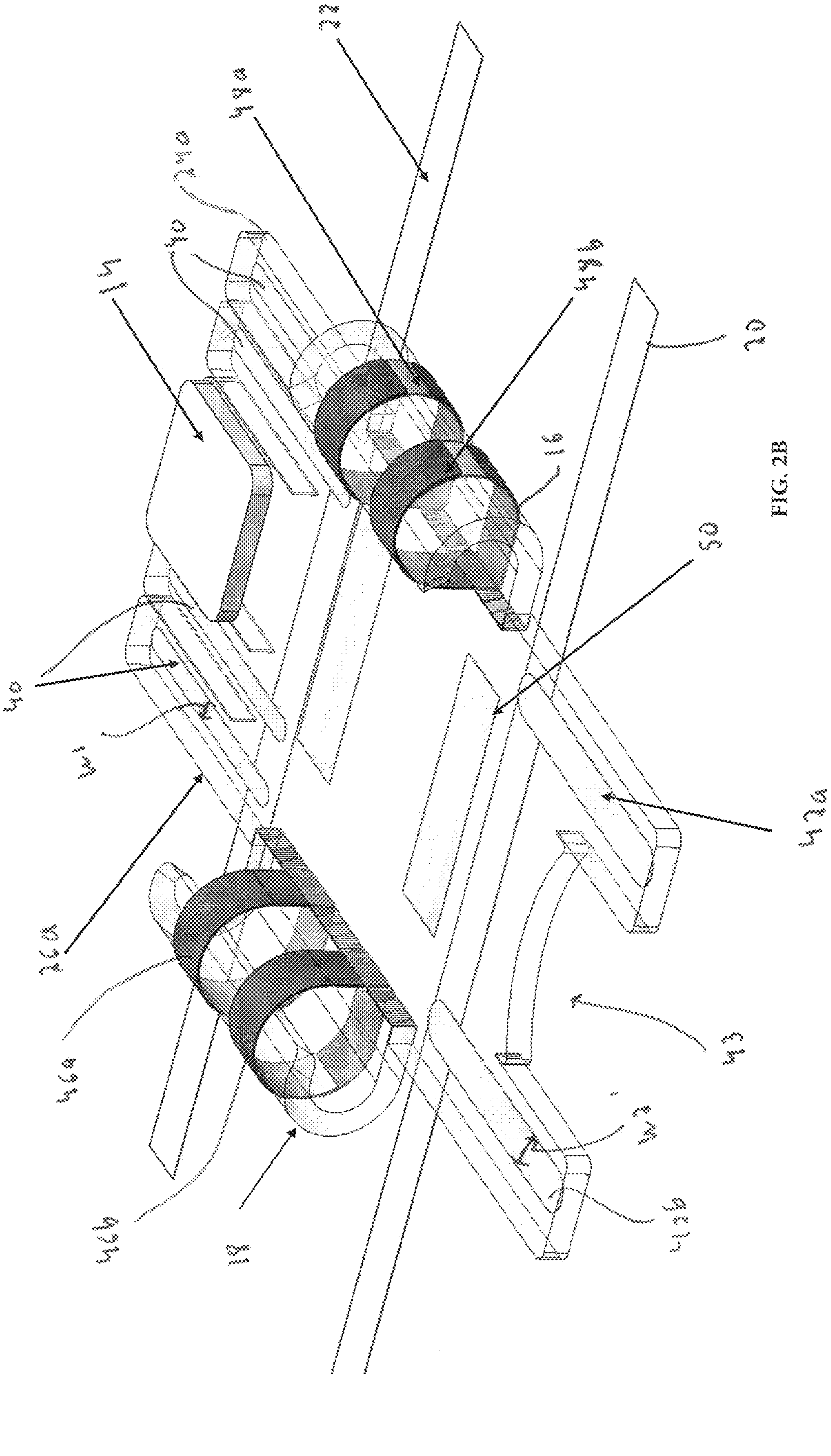
FIG. 2B is a view similar to FIG. 2A showing the side arm sections bent and arm straps looped as in FIG. 1A.

The sections 24*a*, 24*b*, 26*a*, 26*b* are shown in the parallel position in FIGS. 1A, 2A and 2B. In this parallel position, these sections 24*a*, 24*b*, 26*a*, 26*b* are linear/non-bent extending in the same plane as the base 12. In some embodiments, each of the sections 24*a*, 24*b*, 26*a*, 26*b* are additionally or alternatively bendable downwardly to wrap around the operating table, e.g., a rail, to help secure device 10 to the operating table. In some embodiments, the sections 24*a*, 24*b*, 26*a*, 26*b* are additionally or alternatively bendable upwardly to provide a contact portion for the shoulders of the patient, and can be rolled as shown in FIG. 1D to provide a contact/abutment section for the patient. In some embodiments, the outer sections 24*a*, 26*a* are bendable downwardly to attach to the operating table and the inner sections 24*b*, 26*b* are rollable upwardly for shoulder contact/abutment. In alternate embodiments, the inner sections 24*b*, 26*b* are bendable downwardly to attach to the operating table and the outer sections 24*a*, 26*a* are rollable upwardly for shoulder contact/abutment. Note the sections 24*a*, 26*a*, 24*b* and 26*b* can be formed such that they are each independently bendable upwardly or downwardly as decided by the clinician for table securement or patient shoulder contact; in other embodiments the sections 24*a*, 24*b*, 26*a*, 26*b* can be formed so that one or more of the sections can only be bent upwardly and one or more of the sections can only be bent downwardly. In still other embodiments, one or more of the sections 24*a*, 24*b*, 26*a*. 26*b* are not bendable and remain in the straight (planar) position. Stated another way, in the embodiment of FIG. 1A, all of the four sections 26*a*-26*d* are bendable upwardly or downwardly, however, it is also contemplated that one or more of the sections 26*a*-26*d* could be designed to bend only downwardly or only upwardly. It is also contemplated that in some embodiments, less than all the sections 26*a*-26*d* are bendable upwardly and/or downwardly. It is also contemplated that the bendable sections 26*a*-26*d* are not all bendable independently, but one or more sections are bendable together. Metal strips described below support the bendable sections 26*a*-26*d* to help maintain the sections in the bent position.

Figure 1C:
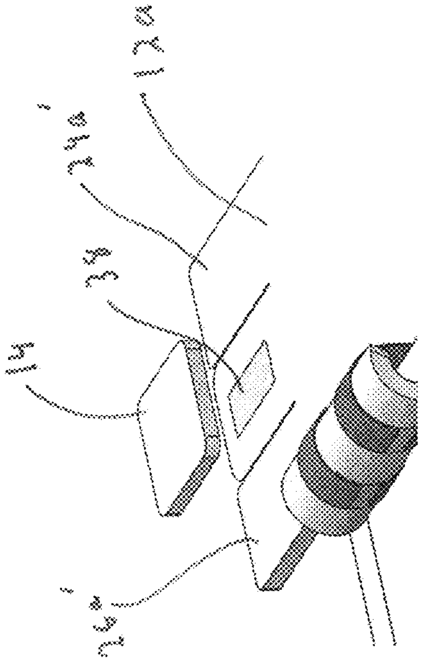
FIG. 1C illustrates the head piece of FIG. 1B being removed for repositioning on the base of the device.
Figure 1B:
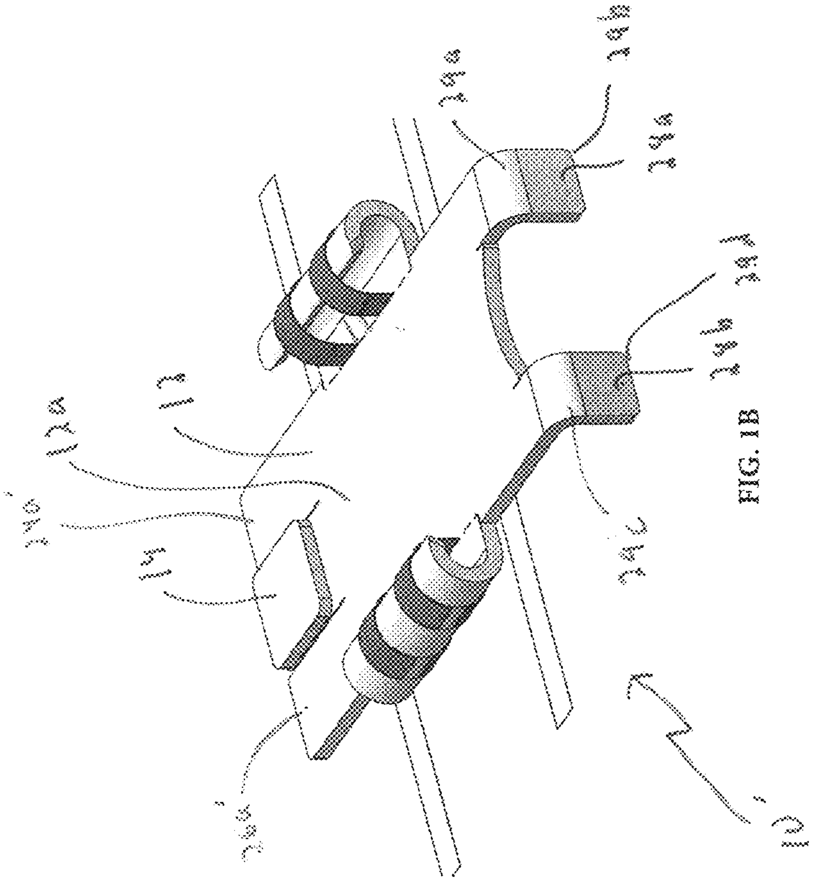
FIG. 1B is a perspective view of an alternate embodiment of the patient positioning device of the present invention having a base with a single left and right top bendable portion (shown in the unbent position), and further showing the lower bendable portions bent downwardly.

In an alternate embodiment, instead of a pair of sections on opposing sides of the head rest 14, a single section is shown on each side of the head rest 14 as depicted in FIGS. 1B and 1C. More specifically, device 10' of FIGS. 1B and 1C is identical to device 10 of FIG. 1A except instead of two sections 24*a*, 24*b* and 26*a*, 26*b* on each side of head rest 14, a single section 24*a'* is on the left side of head rest 14 and a single section 26*a'* is on the right side of the head rest 14, the sections 26*a''*, 26*b''* bendable downwardly for table attachment and/or upwardly for patient support. In all other respects, device 10' is identical to device 10, e.g., base 12, bendable bottom sections 28*a*, 28*b*, etc., and therefore all other features/functions of device 10, including alternatives, are fully applicable to device 10' and for brevity are not further discussed herein.

FIGS. 1A, 2A and 2B show the sections 24, 26 in the flat parallel (non-bent) position. Each bendable section 24*a*, 24*b*, 26*a*, 26*b* includes a bendable metal strip 40, embedded (captured) inside the foam, shown in the transparent view of FIG. 2A. The metal strip 40 maintains the respective bendable section 24*a*, 24*b*, 26*a*, 26*b* in the bent position when bent. In some embodiments, the metal strips 40 are 0.032 inches thick, although other dimensions are also contemplated. Note that in the absence of such metal supports, the foam material would not stay in the bent position and tend to return toward or to the straight/non-bent position of FIG. 1A. FIG. 1D shows the outer sections 24*a*, 24*b* in the downwardly bent position and inner sections 24*b*, 26*b* in the rolled position as an example of one use of device 10. Note the metal strips 40 in the illustrated embodiment have a width W1 less than the width W2 of metal strips 42 of extensions 28*a*, 28*b* (see FIG. 2B) due to the different widths of sections 24*a*, 24*b*, 26*a*, 26*b* and extensions 28*a*, 28*b*. However, in alternate embodiments, the metal strips 40, 42 can have the same dimensions or different dimensions relative to one another. Note that in alternate embodiments, not all of the sections 24*a*, 24*b*, 26*a*, 26*b* would have metal strips embedded therein depending on the desired use of the device.

Note the metal strips 40 and 42 in the illustrated embodiments, are positioned inside cutouts in the foam material so they are retained within the foam material. Alternatively, the foam base 12 can comprise two layers of material with the metal strips positioned between the two layers, and then the two layers secured together, with the metal strips maintained therebetween. The two layers can be the same foam material or the additional layer to sandwich the metal strip between the two layers can be of a different material than the foam material. The two layers can have the same thickness or different thicknesses.

The head rest 14, as noted above, in preferred embodiments, is removably attached to the upper surface 12*a* of the base 12 at the top portion thereof. The head rest 14 forms a cushion for the patient's head. It can be attached to the base 12 by Velcro, although other methods of attachment are also contemplated. The head rest 14 can be positioned at various positions along the longitudinal axis L to adjust for patients of different heights, e.g., for smaller patients, the head rest 14 would be attached closer to the middle portion (midpoint) of the device 10. FIG. 1C illustrates Velcro or Velcro friendly strip 38 for attachment of head rest 14, which has a Velcro strip on its underside to attach to Velcro strip 38. Such Velcro strips (or other attachment methods) can be utilized with the embodiment of FIG. 1A for attaching the head rest. The mounting/attachment strips can be of a different size than shown and more than one strip 38 can be provided. Alternatively, a Velcro friendly covering material can cover a portion of the base 12 in the manner discussed below in the embodiment of FIG. 11, i.e., Version II, to provide a wider surface area for head rest attachment.

Figure 5:
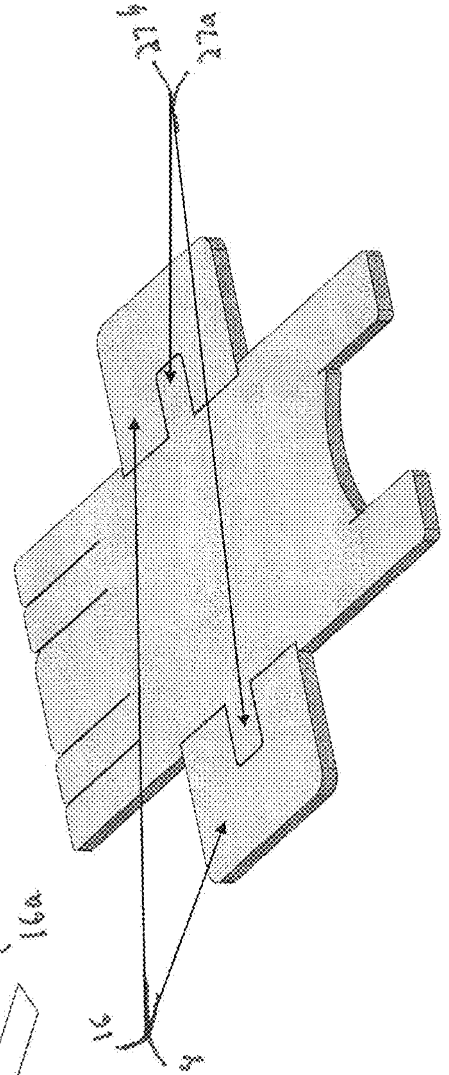
FIG. 5 is a top perspective view of the device of FIG. 4 with the arm straps and head rest removed for clarity.
Figure 4:
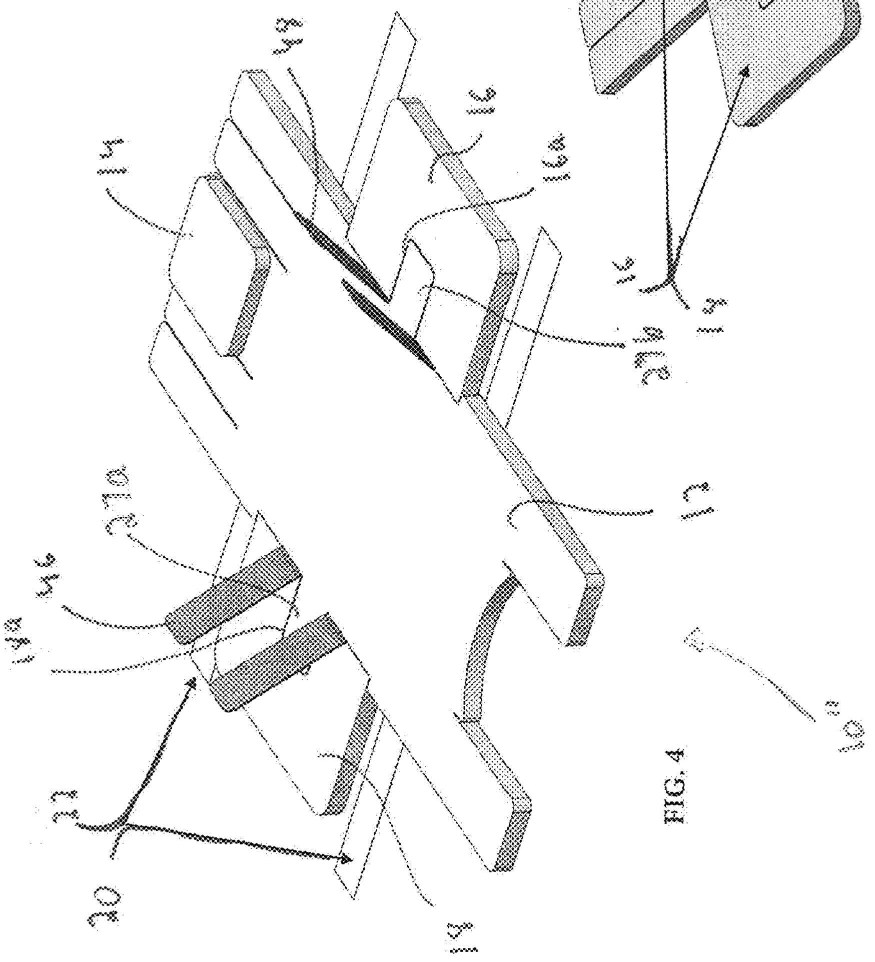
FIG. 4 is a top perspective view of an alternate embodiment of the device of the present invention showing the arm straps in the upward position and the side arm sections in the planar position.

Left and right arm extensions 16 and 18 can be integral with the base 12, however, in alternate embodiments they can be removably attached to the base as shown in FIGS. 4 and 5. More specifically, the extensions 16, 18 of positioning device 12' include side center extensions 27*a*, 27*b*, extending from middle (center) portions of the base 12' and can be bent upwardly or downwardly. Left and right arm sections/extensions 16, 18 each have Velcro strips 54, 55, respectively (FIG. 3). A metal strip 44 (FIG. 2A), extending transverse to the longitudinal axis L, and embedded in the foam base 12, maintains the side extensions 16, 18 in the bent position out of the plane of the base 12 as it wraps around the bent arm section. The arm sections 16, 18 can be bent upwardly to assist holding the patient on the base 12 or bent downwardly to wrap around the OR table to secure the sides of the base 12 to the operating table. FIG. 1A shows one such configuration which the arm sections 16, 18 can be bent into, although other configurations are also contemplated. Note the arm sections 16, 18 are preferably bent once they are attached to the base 12. The side extensions 27*a*, 27*b* of base 12 are each configured to fit within the cutout region of the arm sections 16, 18, respectively, providing an interference fit for attachment for the arm sections to the base.

Figure 6:
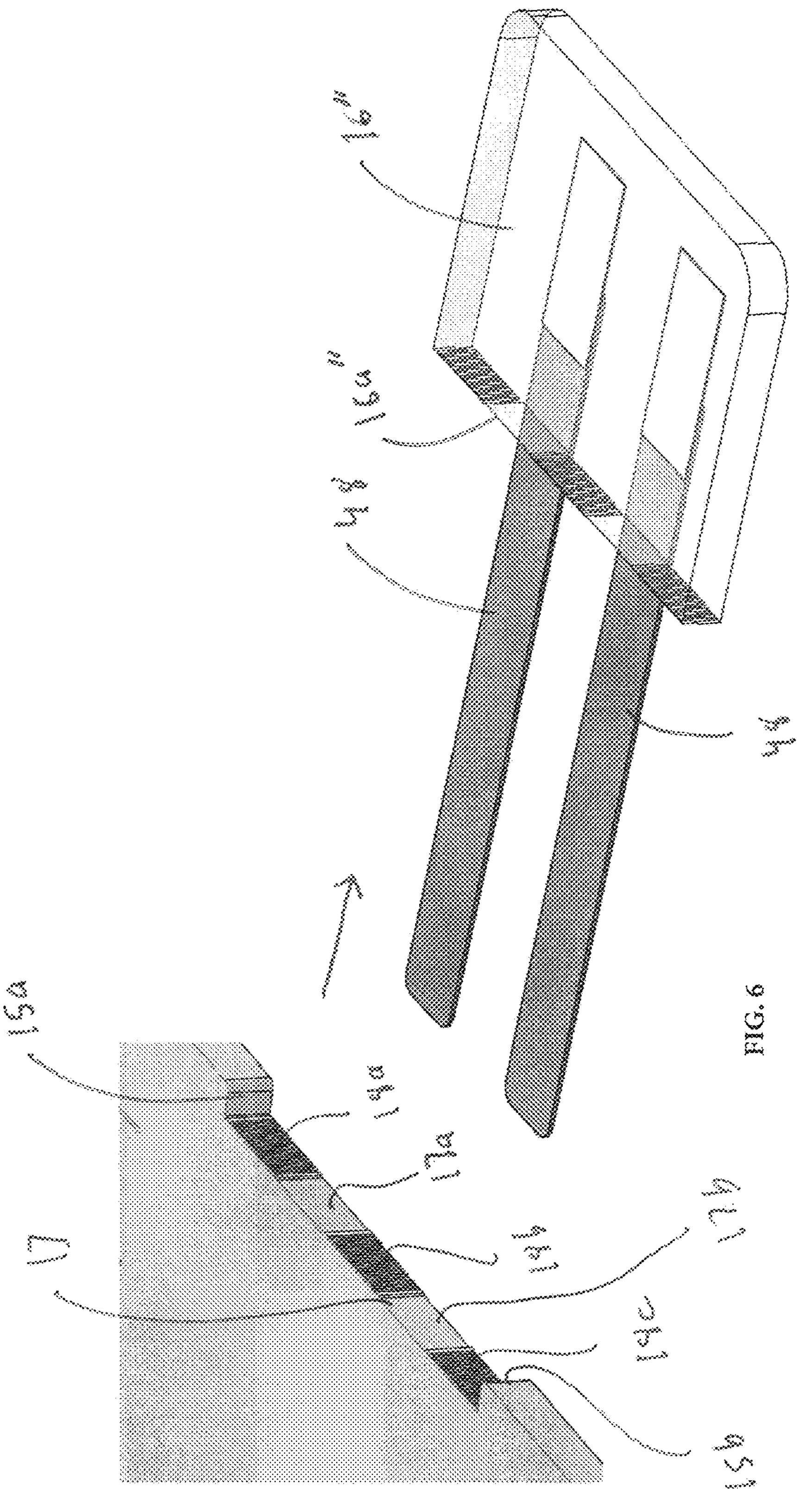
FIG. 6 is a perspective view showing detachment of one of the side arm rest sections from the base of the device of FIG. 1A.
Figure 8:
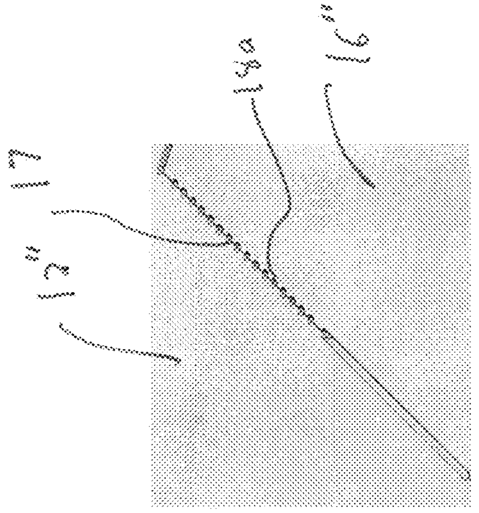
FIG. 8 is a close-up view of the area of detail identified in FIG. 7 showing the tear apart connection of the side arm section and base.
Figure 9:
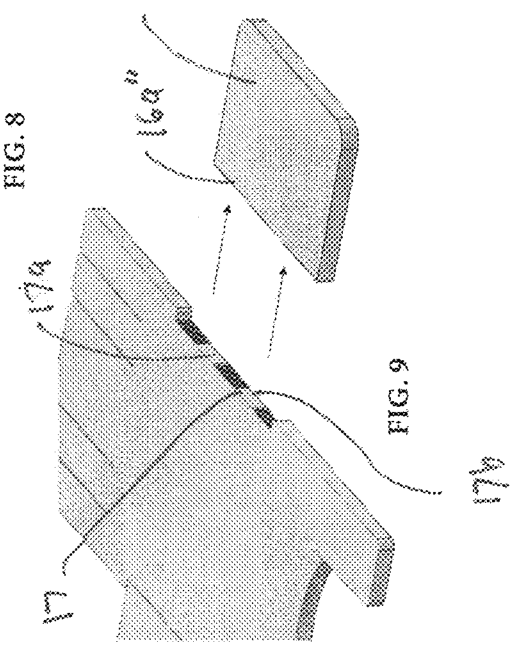
FIG. 9 is a perspective view showing the left arm section being detached from the base of the device of FIG. 7.
Figure 7:
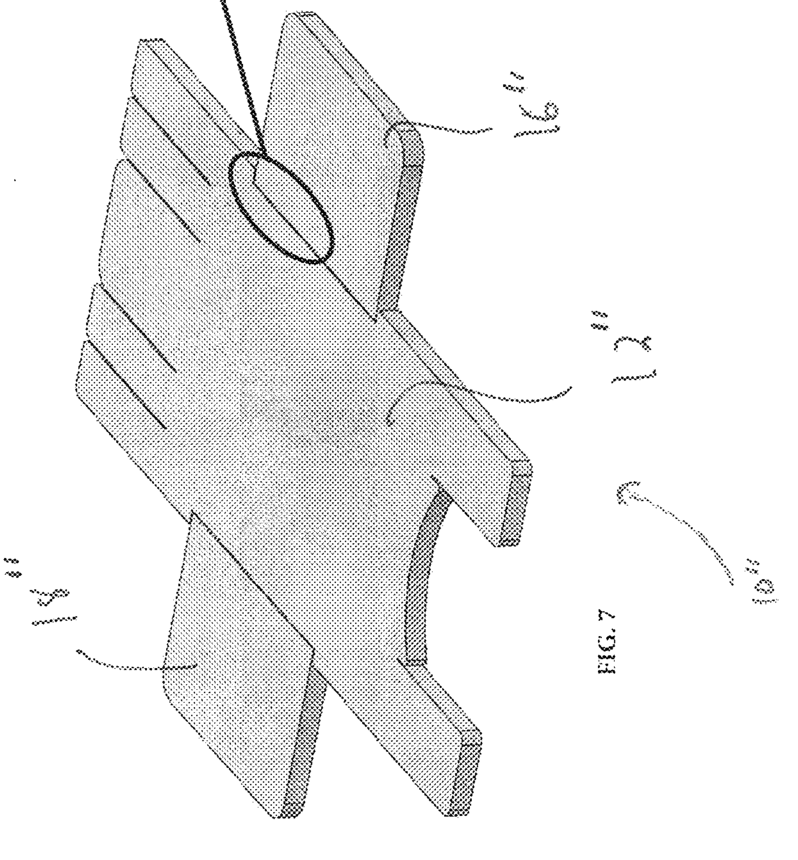
FIG. 7 is a perspective view showing the side arm sections attached to the base of the device of FIG. 1A.

One alternate method of detachment/attachment of the side sections to the base is shown in FIGS. 6 and 7. Side section 16" is shown in these Figures, it being understood that side section 18" could be attached/detached in a similar manner. Side section 16" of device 10" has a tear apart edge cooperating with the right side edge 17 of base 12". There are three tear apart sections shown, designated 18*a*, 18*b* and 18*c*, and collectively referred to as tear apart section 18. The tear apart sections 18*a*, 18*b*, 18*c* are spaced apart to leave a space for the straps 48 which extend through the gap between the inner edge 16*a*" of side section 16" and the outer edge 17 of base 12". That is, gap 17*a* between tear apart sections 18*a* and 18*b* enables passage of one of the straps 48 through the foam and gap 17*b* between tear apart sections 18*b* and 18*c* enables passage of the other strap 48 through the foam. Note edge 17 forms a slight cavity between walls 15*a* and 15*b* dimensioned to create a region for receiving the side section 16". Preferably the left side section 18" and left side edge of the base 12" are the same as the right side section 16" and right side edge of the base 12" and engage and detach in the same manner as side section 16." Straps 46 would extend through the regions devoid of tear sections in the same manner as straps 48.

Note in the embodiment of FIGS. 4 and 5 which have the extensions 27*a*, 27*b*, the side sections 16, 18 in alternate embodiments can have tear away features to separate in the same manner as in FIGS. 6 and 7 or can rely solely on separation of the frictional engagement, i.e., separating the interference fit of the extensions 27*a*, 27 with the respective side section.

With reference to FIGS. 1A and 2A, the left side section 16 and a right side section 18 which provide arm rest pieces for the patient's left and right arms (and thus also referred to herein as left and right arm sections 16, 18), respectively, and help cradle the patient, are shown in the non-bent planar position in FIG. 2A and the bent position in FIG. 1A. As discussed above, in preferred embodiments, including the illustrated embodiment, the side sections 16 and 18 are removably attached to the base 12 via an interference fit (with side extensions/side tabs 27*a*, 27*b*) or other methods of attachment. Attached to left side section 16 are two straps 48 and attached to right side section 18 are two straps 46. The straps 44, 46 in preferred embodiments remain with the side sections 16, 18 when the side sections 16, 18 are removed (detached) from the base (as in FIG. 6). Side sections 16 and 18 can be bent upwardly or downwardly with respect to base 12, or can be rolled from a planar configuration (as in FIG. 4) to U-shaped configurations (34, 36) as shown in FIG. 1A. Although two straps for each section 16, 18 are illustrated a single strap or more than two straps are also contemplated.

If the side sections 16, 18 are bent into a U-shape as shown in FIG. 1A, they can be retained by side straps 48 and 46. More specifically, straps 48*a*, 48*b* (collectively straps 48) are wrapped around side section 16 to secure the side section 16 in the bent position. The straps 48*a*, 48*b* each have a Velcro portion to attach to the Velcro 54 (FIG. 3) on the underside of section 16. The straps 48 extend in a cutout or space between the base 12 and side section 16 and thus can come up from an underside of the side section 16, through a gap between the side section 16 and side edge of the base and then wrap around the bent section 16 to attach to the Velcro section 54. Similarly. straps 46*a*, 46*b* (collectively straps 46) are wrapped around side section 18 to secure the side section 18 in the bent position. The straps 46 each have a Velcro portion to attach to the Velcro 55 (FIG. 3) on the underside of section 18. The straps 48 extend in a cutout or space between the base 12 and adjacent side section 18 and thus can come up from an underside of the side section 18, through a gap between the side section 18 and adjacent side edge of the base and then wrap around the bent section 18 to attach to the Velcro section 55.

Device 10 further includes transversely extending bed straps 20 and 22 which are connected to the base 12 and are used to attach to the bottom of the operating table. These straps 20, 22 can include a Velcro portion to which one end of the strap attaches when it is wrapped around the table. Other forms of attachment are also contemplated. The straps 20, and 22 can also be used in the opposite direction i.e., wrapped around the patient positioned on the base 12 and can be secured by Velcro or other attachment structure. Although two straps 20, 22 are illustrated, a single strap or more than two straps are also contemplated for wrapping around the operating table and/or patient.

Hydrogel pads 50 and 52 attached to the underside of the base 12 (FIG. 3) can be provided to add to the coefficient of friction of the base 12 to reduce sliding of the positioning device 10 on the operating tables as the pads 50, 52 lie atop and in contact with the table 12. The hydrogel pads can also be provided on the top surface of the positioning device 10 in direct contact with the skin to provide skin protection.

The pad in some embodiments can include slits formed therein. Such spaced apart slits can be provided in select regions of the pad to contour to get it to arc better. These select cuts allow select regional adjustments to the base foam compliance. For example, slits in the lumbar region would allow more compliance (ability to conform to shape and reduce pressure regions) compared to regions without slits. Thus, the slits provide different zones to provide different compliance to provide different response to loads. The slits can also aid in bending of the pad.

The bases/pads of the present invention can be asymmetrical. Alternatively, they can be left/right symmetrical as in the embodiment of FIG. 1 or fully symmetrical (left/right and top bottom) as in the embodiment of FIG. 11 discussed below.

FIGS. 11-16 illustrate an alternate embodiment of the device of the present invention. This device as referenced above is the modular attachment version—Version II. This device differs from the device in FIG. 1 in that a) it has a Velcro friendly covering material over the base/pad to enable attachment of supports anywhere on the base and is not limited by the location of the specific placement of the pre-attached Velcro strips; b) supports of various shapes and sizes can be removably attached throughout the pad (via the Velcro friendly cover); c) a metal support extends along a length and width of the foam pad to provide attachments to the operating table/bed; and; d) it has a full symmetric design so the pad can be used in either orientation. Note that the positioning devices of the present invention can have all of the foregoing features a-d, or fewer than all such as one or two of these features, and still provide advantages over current patient positioning devices.

Also, in some embodiments, the positioning device has a double layered pad design as described in detail below which adds additional symmetry by enabling the device to be used effectively on either side, as described below.

Figure 10:
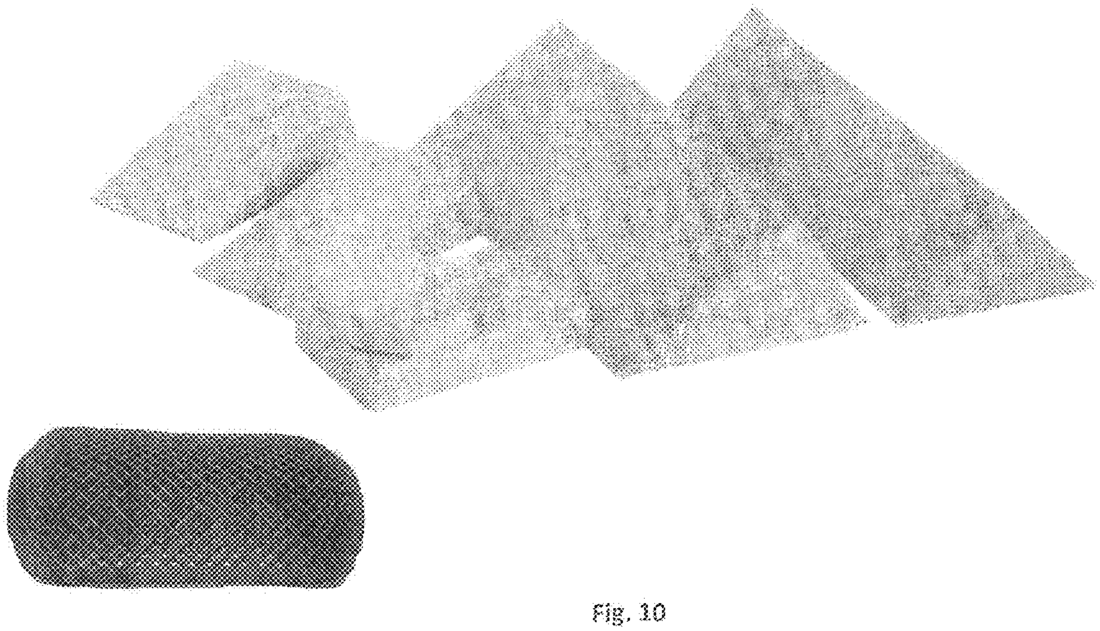
FIG. 10 is a perspective view of examples of various shaped supports or modules which can be used for positioning regions of the body such as body extremities.
Figure 11:
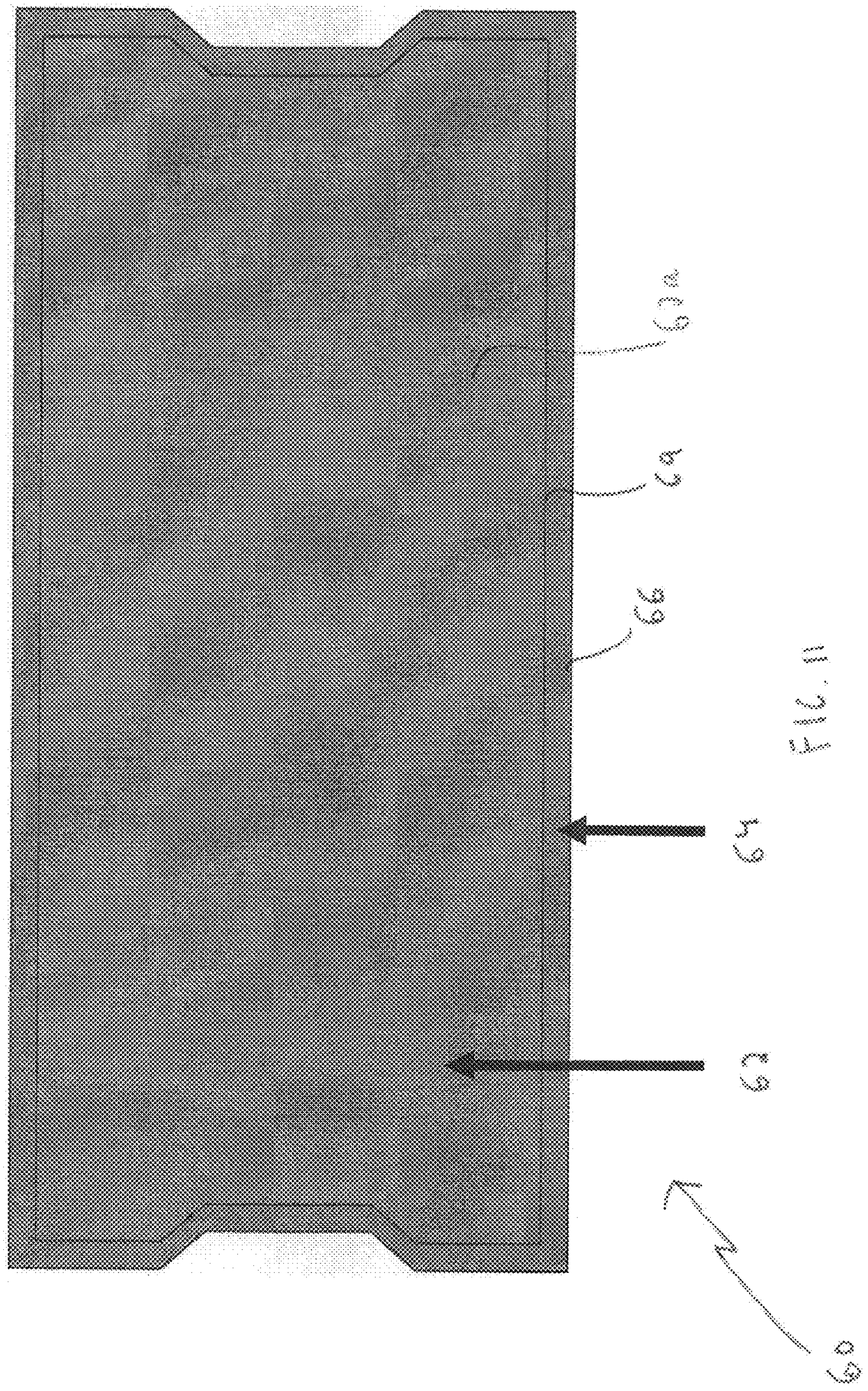
FIG. 11 is a bottom view of an alternate embodiment of the device having a foam core (base) covered by a Velcro friendly layer (metal H-support not shown)
Figure 12:
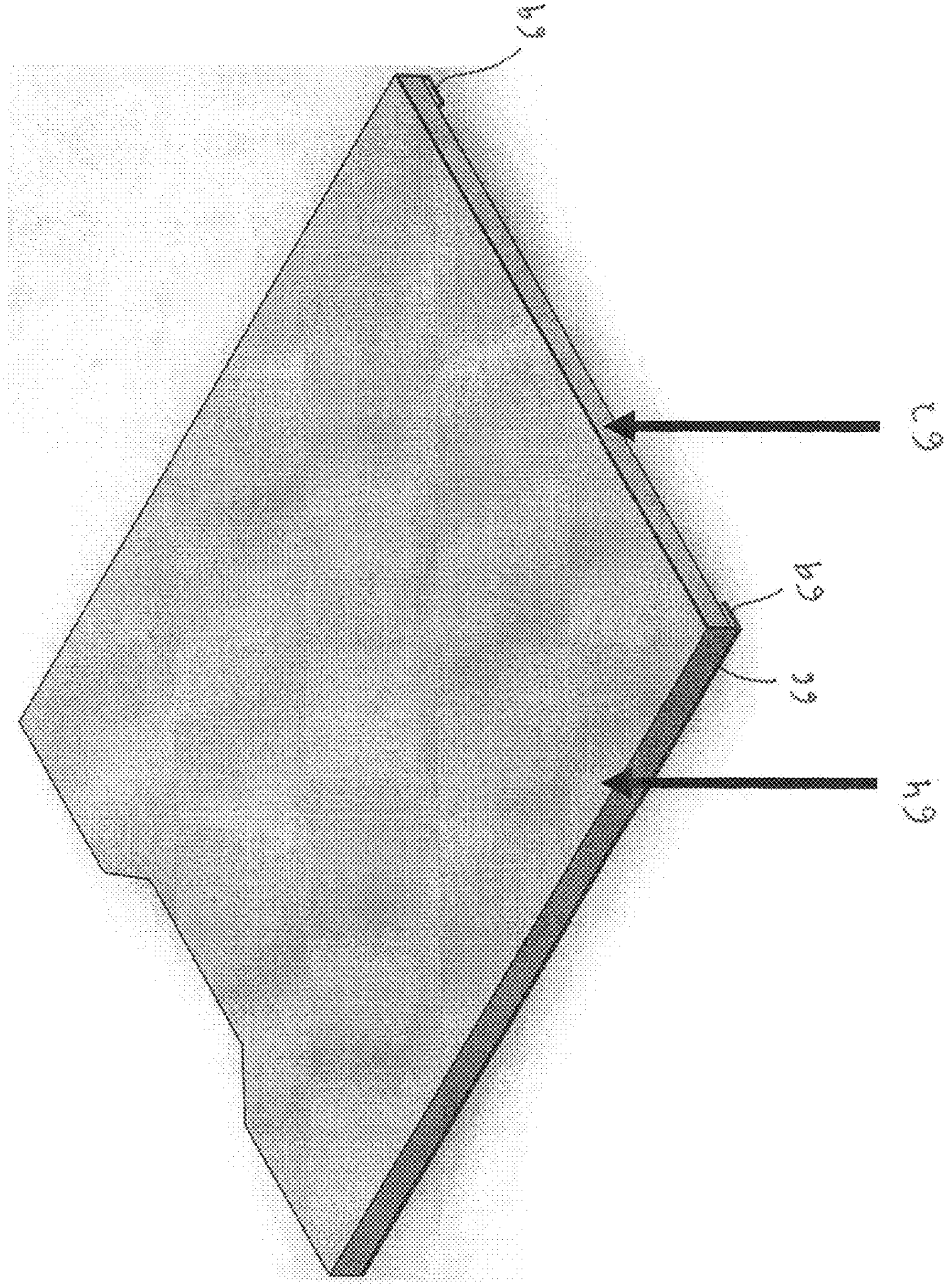
FIG. 12 is a transverse cross-sectional view of the device of FIG. 11 showing the base and covering layer.

Turning now initially to FIGS. 11 and 12, the device, designated generally reference numeral 60, has a pad 62, preferably composed of foam like pad 12 of FIG. 1, (although other materials are contemplated) which is covered or substantially covered by a Velcro friendly material 64 to provide a Velcro attachment surface. In the foregoing embodiments, the pad included Velcro strips at select regions for attachment of the supports or modules, e.g., head rest and arm extensions, and could further include other Velcro strips (not shown) at the appropriate region for attachment of other supports or modules such as lumbar support, shoulder support, shoulder stop, back stop, etc. However, the Velcro friendly material of device 60 of the embodiment of FIG. 11 enables the supports or modules, such as those shown in FIG. 10, e.g., shoulder, head, neck, lumbar, etc. support, to be attached anywhere on the base/pad and thus are not limited by the location of the specific attached Velcro strips as for example in the embodiment of FIGS. 2A and 2B discussed above.

As shown, the material 64 covers the entire top surface of the base 62, and can wrap around the peripheral edge 66 of base 62 forming a lip 69 extending around the periphery (partially or alternatively around the entire periphery as shown in the illustrated embodiment) for better securement. Note alternatively the material can wrap around the bottom surface 62*a* of base 62 to greater extent than shown and in some embodiments can wrap around the entire base (the entire top and bottom surface) to fully encapsulate the base 62. In the illustrated embodiment, since the cover 64 only wraps around the edge, bottom surface 62*a* is exposed. In other embodiments, the material 64 covers only a portion, e.g., a majority portion of the top surface, but not the entire portion of the top surface of the base. The cover material 64 can be attached to the pad by adhesive, laminated, sewn into the foam material or by other attachment methods. The cover material also provides a smooth skin-friendly interface with the patient.

The covering material can also enable incorporation of a logo or other indicia into the material to identify the device, manufacturer, or provide other information.

Figure 13:
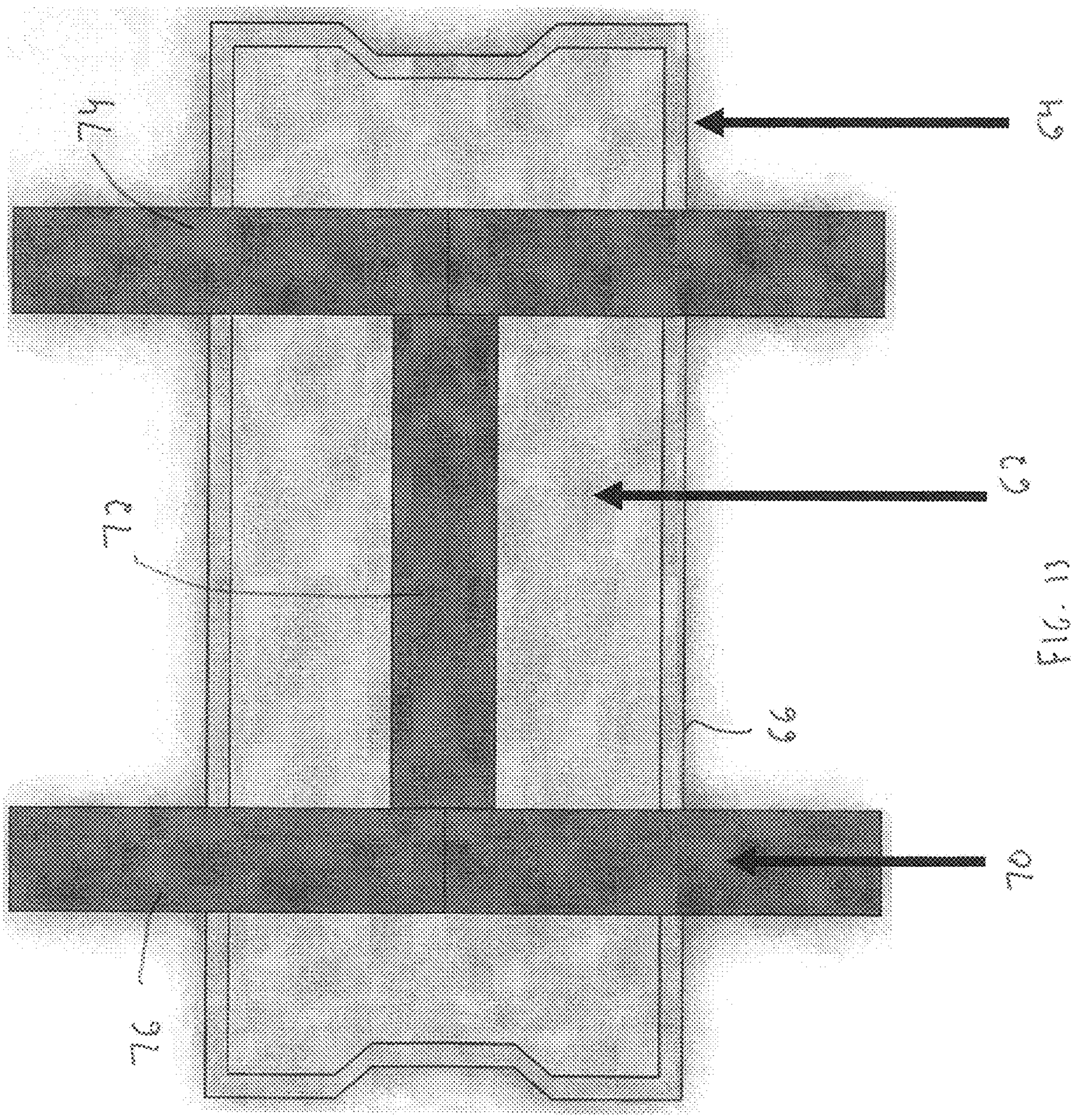
FIG. 13 is a bottom view of the device of FIG. 11 showing one embodiment of a metal support attached thereto.
Figure 14:
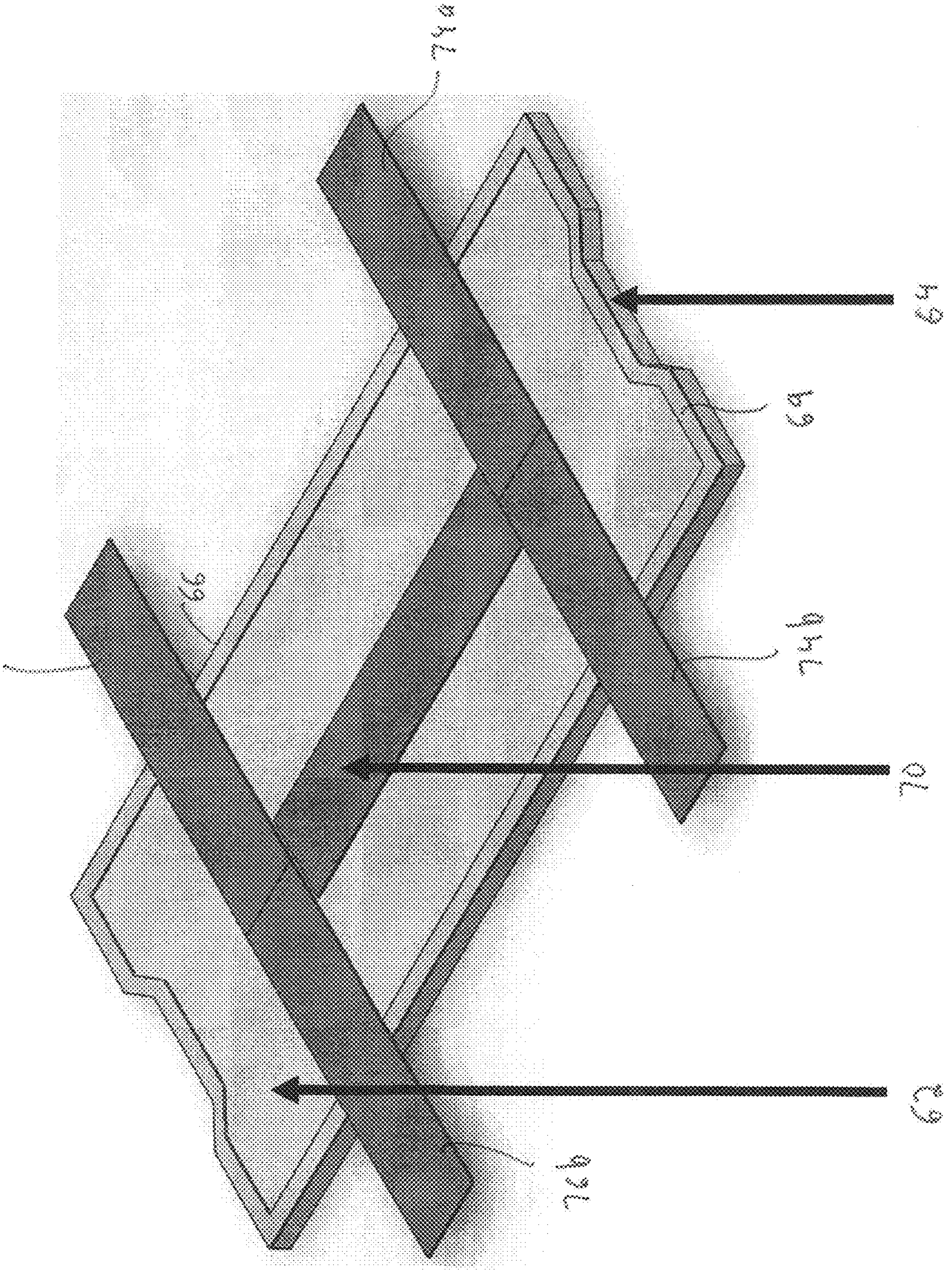
FIG. 14 is a bottom perspective view of the device of FIG. 13.

The device 60 further includes a metal support or splint 70 extending along a substantial length and/or width. The support 70 can be in shape of an H as shown in FIG. 13, the shape of a Figure eight, an X, or other shapes to extend along the pad. With the H-shape, metal support portion 72 extends along a length, i.e., along a longitudinal axis of the base 62, and has two axially spaced apart metal support portions 74, 76 extending transversely to the longitudinal portion 72. Support portions 74, 76 can be at 900 angles to the longitudinal portion or at other angles. Note the metal support 70 can be composed of a single piece of metal or alternatively composed of multiple pieces of metal attached together, e.g., supports 74, 76 attached to support 72, support 74 composed of two or more pieces attached together, etc. The metal 70 is bendable out of the plane so it can be used to wrap around the bar or rail of the operating table to provide rigid fixation to the table. The metal support 70 is shown in the non-bent planar position in FIGS. 13 and 14. Note in alternate embodiments, only one transverse support portion could be provided or more than two transverse support portions can be provided axially spaced along the longitudinal axis. The longitudinal support 72 and transverse supports 74, 76 can extend for a longer or shorter length than shown in FIG. 13.

Figure 15A:
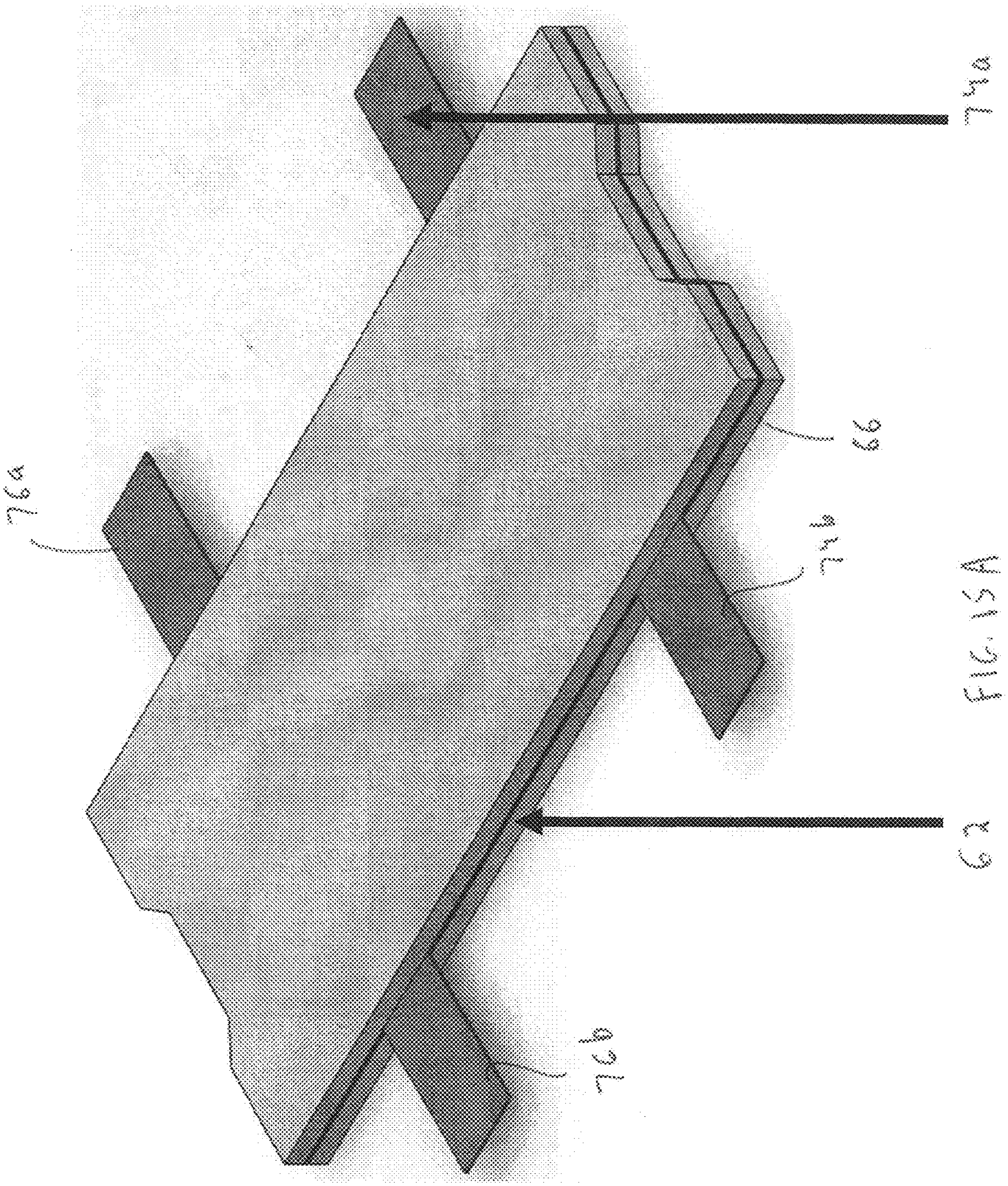
FIG. 15A is a perspective view showing the metal support sandwiched between two foam pads in accordance with a dual layer embodiment.
Figure 15B:
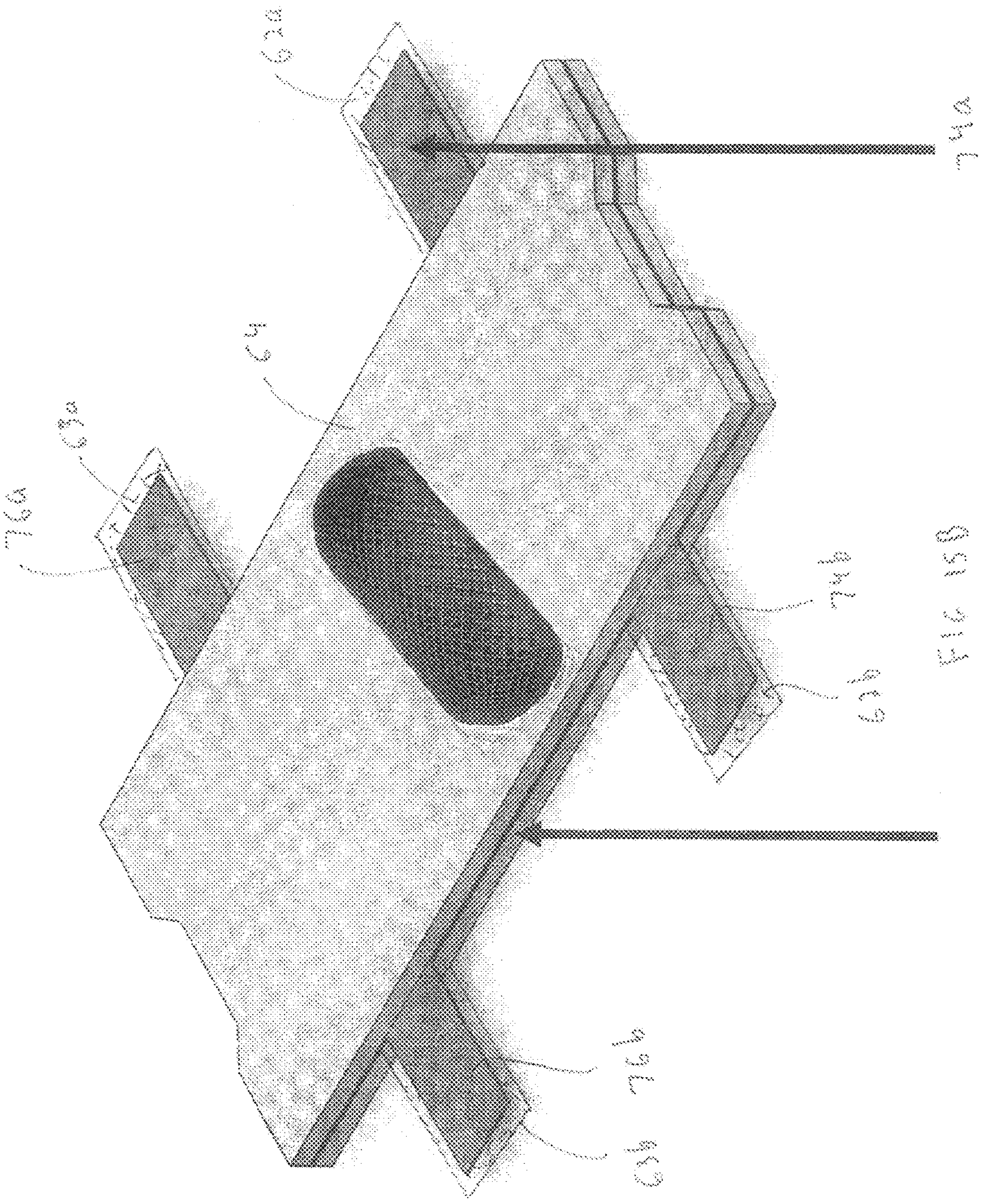
FIG. 15B is a perspective view similar to FIG. 15A showing the foam pad extending over the extending ends of the metal support and further showing a lumbar support attached to the base via attachment to the covering material.

The ends of the two metal supports 74, 76 extend beyond the periphery 65 of the pad 62 and are of a sufficient length so they can be bent around the table. The extending portions 74*a*, 74*b* and 76*a*, 76*b* are shown exposed in FIG. 15A but in preferred embodiments, extending portions 74*a*, 74*b* are covered by foam extensions 62*a*, 62*b*, respectively, and extending portions 76*a*, 76*b* are covered by foam extensions 63*a*, 63*b*, respectively, as shown in FIG. 15B. The extending portions 74*a*, 74*b*, 76*a*, 76*b* can alternatively be covered by other protective material such as by a rubber spray. One advantage of the metal is that it doesn't twist in the same manner as other material such as Velcro (which can tear) if used as a tension strap. With the metal in the embodiment of FIG. 11 running continuously through the center of the foam pad 62, it can also assist lifting the patient from the surgical table to a transport device for moving the patient.

The metal support can be covered with foam as described above and shown in FIG. 15B or alternatively can be encapsulated or covered in another protective material of a soft membrane to cover any sharp edges. Metals that can be used for example are aluminum (which is radiolucent), copper, stainless steel, etc. The metal selected needs to strike the balance of being sufficiently thick to provide sufficient clamping/retention force on the table when bent around the rail but not too thick which could limit its bendability. The material and thickness of the metal need to strike a balance between these two competing factors.

The pad 62 is shown as a symmetrical design. One advantage of the symmetrical foam pad 62 is that the user does not need to worry about the positioning of the device on the table nor the patient's positioning since the "top" and "bottom" are identical and the right and left are identical. Thus, for example, the head rest can be attached on either the "top" or "bottom" of the foam pad.

Figure 16:
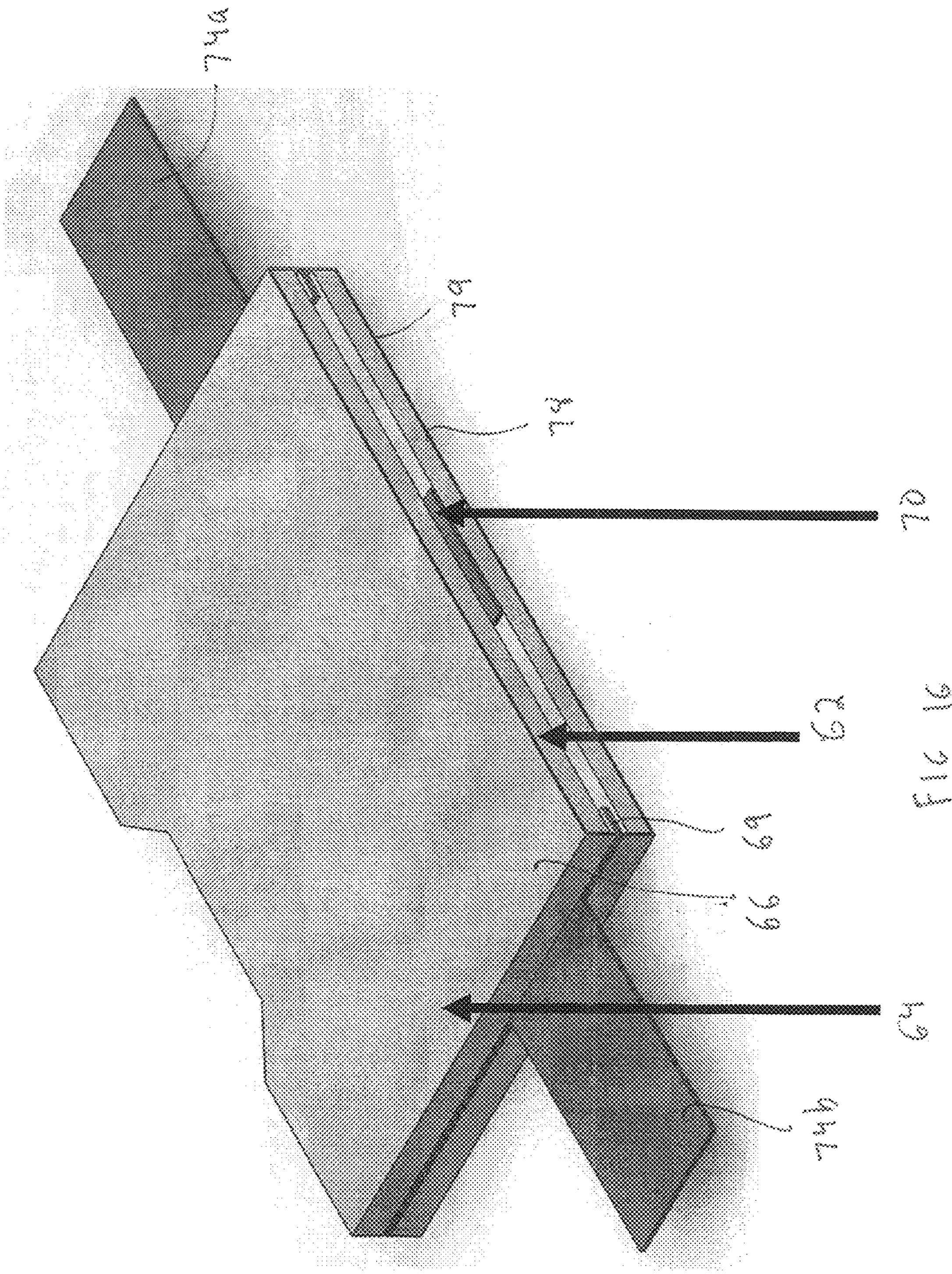
FIG. 16 is a transverse cross-sectional view of the dual layer positioning device of FIG. 15A.

To provide further symmetry, a second pad layer, preferably composed of foam although other materials are also contemplated, can be placed over the first layer as shown in the embodiment of FIG. 16. This provides additional symmetry so the device can be used on either side. As shown, in this double pad design, the metal support 70 is sandwiched between the first foam pad 62 and the second foam pad 78. Foam pad 78 is covered by a Velcro-friendly material 79 in the same manner as foam pad 62, thus forming a four-layer design—material 64, pad 62, pad 78, and material 79. The Velcro material 79, like material 64, can partially or fully encapsulate the foam pad 78 and provides a surface for attachment of the support or modules in the same manner as foam pad 62. In this manner, the device can be used with either covering material 64 or covering material 79 facing the patient with the other material facing the table. Note the discussion above of foam pad 62 and covering material 64, and their alternatives, are fully applicable to foam pad 78 and covering material 79. Pads 62 and 78 can be composed of the same material or a different material.

In some embodiments, to minimize tearing of foam at high stress pints, radial relief cuts are provided and/or non-woven backing material is applied to distribute forces and eliminate tears.

Sections of the devices of the present invention can be absorbent or superabsorbent to absorb blood and/or other body fluids. This absorbability can be part of the foam material itself and/or in form of absorbable inserts placed in and/or on the foam. Alternatively, or in addition, wound care materials, e.g., multi-layer wound dressing, providing a wicking agent and an absorbent can be placed on select regions of the foam or on select regions of the covering material in the embodiments utilizing the Velcro-friendly material, such as in the perineum or sacrum area for example. In some embodiments, a section dressing material can be attached, e.g., by adhesive or placed, e.g., wrapped, over a section of the foam or covering material to provide a high-water absorption rate.

The devices of the present invention can include a lumbar support providing a raised support on the pad. In some embodiments, the lumbar support could have a fluid containment feature, such as pockets, to absorb blood and/or other body fluids.

The positioning devices of the present invention advantageously provide fast setup, e.g., 15 seconds or less, via the bendable sections and/or straps.

The positioning devices in preferred embodiments provide a universal shape. In such embodiments, instead of relying on fixed shapes to position body extremities during surgery, the bendable integrated segment or segments allow for on demand shape contouring. Specifically, the malleable material holds and overcomes deformation loads such that the new deformed shape can support body loads in any geometry, providing a one size fits all technology. Standard and complex shapes, asymmetrical or symmetrical, can be created using the bendable internal segment to hold the shape.

Examples of support or modules are shown in FIG. 10 which include for example shapes that are right-triangular in cross-section, equilateral-triangular in cross-section, circular in cross section, rectangular in cross-section, oval in cross-section (lumbar support), etc. These patient supports can be part of the pad or separate connectable components permanently or removably attached to the pad or covering material in the embodiments utilizing the Velcro-friendly covering material or Velcro strips.

The bendable metal segment(s) in some embodiments enables the flat sheet of foam to morph into different shapes such as triangles, rectangles, domes, etc. and hold the shape. It is also possible in some embodiments to cut the foam and bendable segment(s) to various shapes to support various body parts. For example, the sheet of bendable foam could be bent into a box and hold its shape to support the knee, bent into a pyramidal shape, etc.

Although the positioning devices are described for use with an operating table to overlie the operating table or bed, they can also be used to support patients on other patient supporting structure. Thus, the term "patient supporting structure" as used herein is not limited to operating/surgical tables.

Note the supports described herein can be attached/attachable directly to the base or attached/attachable to the base via a covering material interposed between the base and covering material. In either case, the supports are considered herein to be "attached/attachable to the base." They are preferably removably attachable.

The devices in some embodiments are packaged sterile; in other embodiments they are packaged non-sterile.

In some embodiments, the devices can be vacuum packaged to reduce shipping size (and cost) such as by way of example 50% or 66%, or by other sizes/percentages. In such embodiment, the permeable bag is first subject to the sterilization agent (ETO), and subsequently (after the sterilization cycle has been completed) a second vacuum bag is used to compress the foam using atmospheric pressure without violating the sterile barrier for reduced size vacuum packaging. In an alternate embodiment, the device is mechanically compressed prior to sterilization, and then ETO sterilized in a compressed (reduced size) state. In some embodiments, the vacuum compression or the mechanical compression can reduce the size for shipping by a 3 to 1 ratio.

The devices of the present invention can be designed for single use. In other embodiments, they can be designed for multiple uses after sterilization between each use. In embodiments, wherein the pad has a cover, the pad can be reusable and the cover can be disposable. In such embodiments, the cover can be removed and a new sterile cover can be placed over the pad. In other embodiments, with a covering material, multi-layers of covers can be provided, so that after each use, the topmost cover is removed leaving a clean sterile cover exposed for use. In such embodiments, the covers would preferably cover the entire pad (top, bottom, sides) to maintain the underlying pad portion sterile.

In an alternate embodiment, the device can be attached to the operating table by wrapping it with a material such as Coflex. In such embodiments, instead of the bendable metal or foam wrapping around the table, such bendable regions need not be provided in the device and attachment can rely solely on the wrapping the material one or more times around the device and table. This could provide an easier to manufacture and less costly positioning device.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure.

Although the apparatus and methods of the subject invention have been described with respect to preferred embodiments, which constitute non-limiting examples, those skilled in the art will readily appreciate that changes and modifications may be made thereto without departing from the spirit and scope of the present invention as defined by the appended claims.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the above description, terms such as "approximately," "about", "generally," "substantially," and the like should be understood to allow for variations in any numerical range or concept with which they are associated. It is intended that the use of terms such as "approximately", "about", "substantially", and "generally" should be understood to encompass variations on the order of 25%, or to allow for manufacturing tolerances and/or deviations in design.

Where a range of values is provided, it is understood that each intervening value, between the upper and lower limit of that range is encompassed within the invention.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present invention.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A patient positioning device attachable to a medical table, the patient positioning device comprising:

a) a base having an upper surface configured for engagement with a patient, a lower surface, a top region at a first portion, a bottom region at a second portion, a right side region and a left side region, the base configured to overlie the medical table and underlie a patient, wherein the upper surface faces the patient and the lower surface faces the table the upper surface including a fastener system; and b) at least two differently configured patient supports removably attachable to the base to underlie to support a body regions of the patient, the at least two differently configured supports each attachable to a plurality of selective regions of the upper surface of the base to selectively vary locations of attachment of the at least two differently configured supports, each of the at least two differently configured supports providing a raised surface from the upper surface of the base and configured for engagement with the patient.

2. The positioning device of claim 1, wherein the at least two supports include an arm rest removably attachable to one or both of the right or left side regions of the base.

3. The positioning device of claim 1, wherein the at least two supports include a head rest removably attachable to the top region of the base.

4. The positioning device of claim 1, wherein the base is made of a foam material and one or more portions of the base are bendable to form one or more bendable portions for attachment to a rail of the medical table.

5. The positioning device of claim 1, wherein the at least two supports include a lumbar support.

6. The positioning device of claim 1, further comprising a metal support attached to the base, the metal support bendable to attach to the medical table.

7. The positioning device of claim 6, wherein the metal support extends beyond right and left sides of a periphery of the base and are covered by a protective material.

8. The positioning device of claim 6, wherein the metal support comprises one or more metal members that extend along a length and a width of the base.

9. The positioning device of claim 1, wherein the base is symmetric so it can be positioned on the medical table in either direction.

10. The positioning device of claim 1, wherein the base includes a covering material covering at least a majority portion of the upper surface of the base to provide a hook and loop fastener friendly material for removable attachment of the supports to the hook and loop fastener friendly material.

11. The positioning device of claim 10, wherein the base forms a first base and the device includes a second base attached to the first base, the first and second bases composed of a foam material and a metal support sandwiched between the first and second bases.

12. The positioning device of claim 11, wherein the second base includes a second covering material covering at least a majority of the upper surface of the second base to provide a hook and loop fastener friendly material for removable attachment of the supports to the hook and loop fastener friendly material if the device is used on a side where the second covering material faces the patient, the first base providing for the removable attachment of the supports if the device is used on a side where the first covering material faces the patient.

13. A patient positioning device attachable to a medical table, the patient positioning device patient comprising:

a) a base having an upper surface having a top region at a first portion, a bottom region at a second portion, a right side region and a left side region, the base configured to overlie the medical table and underlie a patient to provide a support for the patient; and b) first and second differently configured patient supports for selective removable attachment to the upper surface of the base and providing a raised surface from the upper surface of the base and configured for engagement with the patient;

c) wherein the patient supports include the first and second arm supports configured to be open and extending less than 360 degrees about each arm to expose a portion of each arm.

14. The positioning device of claim 13, wherein the upper surface of the base provides a hook and loop fastener attachment surface for the first and second patient supports.

15. The positioning device of claim 13, wherein the base comprises a foam pad having a plurality of slits formed in the upper surface therein to form zones of differing compliance to provide zones of differing response to loads.

16. The positioning device of claim 13, further comprising an absorbent material positioned over the base to provide a high-water absorption rate.

17. A patient positioning device attachable to a medical table, the patient positioning device comprising:

a) a base having a top region at a first portion, a bottom region at a second portion, a right side portion and a left portion, the base configured to overlie the table and underlie the patient to provide a support for the a patient; and b) first and second straps extending transversely across a width the base and beyond a periphery of the base beyond the right side portion and left side portion, the first and second straps configured to wrap in a first direction around the medical table and in a second opposite direction around the patient.

18. The positioning device of claim 17, wherein the base is composed of a foam which includes a plurality of slits formed in an upper surface therein to form zones of differing compliance to provide zones of differing response to loads.

19. The positioning device of claim 17, further comprising a metal support having a first region extending from the top region to the bottom region and a second region transverse to the first region extending from the left side region to the right side region.

* * * * *